United States Patent [19]

Berling et al.

[11] 4,382,924

[45] May 10, 1983

[54] PALATABLE COMPOSITION CONTAINING OIL OR OIL-LIKE MATERIALS

[75] Inventors: Kenneth G. Berling; Thomas G. Crosby, both of Cincinnati, Ohio

[73] Assignee: The Procter & Gamble Company, Cincinnati, Ohio

[21] Appl. No.: 162,961

[22] Filed: Jun. 25, 1980

[51] Int. Cl.³ .................. A61K 31/72; A61K 31/225; A61K 31/23; C07H 13/04
[52] U.S. Cl. .................................. 424/180; 424/312; 424/313; 536/119; 536/63; 426/548; 426/601
[58] Field of Search .................. 424/180, 312, 313; 536/119, 63; 426/548, 601

[56] References Cited

U.S. PATENT DOCUMENTS

| | | | |
|---|---|---|---|
| 2,916,416 | 12/1959 | Buckwalter | 167/55 |
| 3,454,405 | 7/1969 | Beach | 99/108 |
| 3,582,336 | 6/1971 | Rasmusson | 99/83 |
| 3,600,186 | 8/1971 | Mattson et al. | 99/1 |
| 3,628,970 | 12/1971 | Stephens | 99/140 |
| 3,743,716 | 7/1973 | Rizzi | 424/49 |
| 3,778,517 | 12/1973 | Neely | 426/175 |
| 3,867,557 | 2/1975 | Neely et al. | 426/175 |
| 3,899,592 | 8/1975 | Suarez et al. | 426/2 |
| 3,968,261 | 7/1976 | Goodman | 426/98 |
| 4,013,801 | 3/1977 | Dawson et al. | 426/548 |
| 4,034,083 | 7/1977 | Mattson | 424/180 |

FOREIGN PATENT DOCUMENTS 2241291  3/1975  France .

*Primary Examiner*—John M. Ford
*Attorney, Agent, or Firm*—M. P. Brennan; S. J. Goldstein; J. D. Schaeffer

[57] ABSTRACT

Pleasant-tasting, non-greasy, edible compositions, preferably in liquid form, comprising edible oil or oil-like materials, a high potency, lipid soluble sweetener, such as saccharin, and a lipid soluble flavorant, are disclosed. These compositions are particularly useful as an oral dosage form for vitamins or pharmaceutical materials; in such embodiments the edible oil-like material may consist, in whole or in part, of an oily pharmaceutical agent, such as polyol fatty acid esters having at least four fatty acid ester groups, each fatty acid having from about 8 to about 22 carbon atoms.

11 Claims, No Drawings

PALATABLE COMPOSITION CONTAINING OIL OR OIL-LIKE MATERIALS

BACKGROUND OF THE INVENTION

The present invention relates to edible compositions which, in spite of the fact that they contain large amounts of oil or oil-like materials, are highly palatable when ingested orally. These compositions are particularly useful as carriers for pharmaceutical agents.

A wide variety of oil and oil-like materials are well-known ingredients in edible products, such as foods or pharmaceuticals. These materials, however, are generally found to be extremely distasteful and difficult to swallow when taken orally. This fact would readily be confirmed by almost anyone who has had to swallow castor oil. While oil can be made relatively bland in taste through deodorization, organoleptically it is still greasy tasting, relatively viscous, and very difficult for most people to stomach. A simple, easy to prepare composition which would remove such negative taste and mouthfeel impressions would, thus, be very useful, for example, in preparing an oral dosage form of oil-like pharmaceutical agents. It has now been found that by combining a high potency lipid soluble sweetener, such as saccharin, and a flavorant with an oil or oil-like material, the resulting edible composition surprisingly does not have an oily or otherwise unpleasant mouthfeel or taste and is quite palatable when ingested orally.

Various edible oils have long been known to be usefully included in food compositions, such as in mayonnaise, various food coatings or toppings, and salad dressings. See, for example, U.S. Pat. No. 3,454,405, Beach, issued July 8, 1969; U.S. Pat. No. 3,582,336, Rasmusson, issued June 1, 1971; U.S. Pat. No. 3,743,716, Rizzi, et al., issued July 3, 1973; and U.S. Pat. No. 3,968,261, Goodman, issued July 6, 1976, all of which are incorporated herein by reference. Some of these oil-containing food compositions additionally include a wide variety of sweetener and flavor components. However, there is no recognition that the selection of a specific subgroup of sweeteners as required in the present application, can, together with lipid soluble flavorants, provide palatable compositions containing high levels of edible oils or oil-like materials.

Numerous sweeteners and flavor enhancers have also been taught in the art. See, for example, U.S. Pat. No. 3,628,970, Stephens, et al., issued Dec. 21, 1971; and U.S. Pat. No. 3,899,592, Suarez, et al., issued Aug. 12, 1975, both of which are incorporated herein by reference. While these sweeteners may be, and frequently are, used in combination with various flavorants, there is no teaching or suggestion of their use with oily materials in the type of compositions taught in the present application. Finally, French Specification No. 73-23422, Laboratoires Sandoz S.A.R.L., published Mar. 21, 1975, describes the use of mixtures of saccharin and flavorant which are incorporated in gelatin capsules in order to mask bad flavors found in certain medicine products; the formation of a palatable edible oil or oil-like material containing compositions is not involved in the invention disclosed therein.

It is, therefore, an object of the present invention to provide an edible composition containing an oil or oil-like material which is found to be palatable and pleasant when eaten.

It is a further object of the present invention to provide a palatable, easy to prepare oral delivery vehicle for oily or lipid soluble pharmaceutical agents.

SUMMARY OF THE INVENTION

The present invention relates to pleasant, non-greasy tasting edible compositions, preferably in liquid form, comprising:
(a) from about 25% to about 99.9% of an edible oil or oil-like material;
(b) from about 0.001% to about 5% of a highly potent lipid soluble sweetener; and
(c) from about 0.1% to about 5% of a lipid soluble flavorant.

In a preferred embodiment, the compositions are used as a oral dosage form of a pharmaceutical agent wherein the edible oil or oil-like material is, at least in part, a pharmaceutical agent, such as polyol fatty acid esters having at least four fatty acid ester groups, each fatty acid having from about 8 to about 22 carbon atoms. The present invention also relates to the process for making the above-described palatable compositions wherein the sweetener is solubilized in the oil or oil-like material, such as by heat and/or agitation, and the flavorant is subsequently added in a manner so as not to lose its volatile components.

DETAILED DESCRIPTION OF THE INVENTION

The compositions of the present invention contain, in major part, an edible oil or oil-like material; thus, the compositions contain from about 25 to about 99.9%, preferably from about 50 to about 99.9%, and most preferably from about 70 to about 99.9% of the oil or oil-like material. Although the present invention is preferably formulated as a liquid, it may also be formulated as a solid (e.g., a solid shortening or margarine) by using a solid or semi-solid fat as the oil-like material. To formulate the preferred liquid execution, the oily material should be one which is liquid at room temperature. Any edible oil which meets these criteria or mixtures of such oils may be included in the compositions of the present invention; examples of such materials include, but are not limited to, vegetable oils, coconut oil, palm oil, cottonseed oil, palm kernel oil, rapeseed oil, corn oil, soybean oil, sunflower oil, and safflower oil.

In addition to such conventional edible oil materials, the oil-like component may be a pharmaceutical agent or a vitamin having an oily character. When such pharmaceutical agents are used, they are incorporated in amounts which are both safe and effective in the treatment of a particular medical condition; the determination of what such amounts are is dependent upon the particular pharmaceutical agent used and is well within the skill of those knowledgeable in the pharmaceutical arts. Preferred examples of such pharmaceutical agents are the polyol fatty acid esters having at least 4 fatty acid ester groups, each fatty acid having from about 8 to about 22 carbon atoms. These materials are known to have efficacy both as low calorie fats and as inhibitors of cholesterol absorption in the body. See, U.S. Pat. No. 3,600,186, Mattson and Volpenhein, issued Aug. 17, 1971 and U.S. Pat. No. 3,954,976, Mattson and Volpenhein, issued May 4, 1976, both of which are incorporated herein by reference. Examples of such compounds include glucose tetraoleate, glucose tetrastearate, glucose tetraester of soybean oil fatty acid, mannose tetraester of tallow fatty acid, galactose tetraester of olive oil fatty acid, arabinose tetraester of cottonseed oil fatty acid, xylose tetralinoleate, galactose pentastearate, sorbitol tetraoleate, sorbitol hexaester of olive oil fatty acid, xylitol, pentapalmitate, xylitol tetraester of substantially completely hydrogenated cottonseed oil fatty acid, sucrose tetrastearate, sucrose pentastearate, sucrose hexaoleate, sucrose octaester of substantially completely hydrogenated soybean oil fatty acid, sucrose octaester of peanut oil fatty acid, erythritol tetraester of olive oil fatty acid, erythritol tetraoleate, xylitol pentaoleate, sorbitol hexaoleate, sucrose octaoleate, sucrose octaester of soybean oil fatty acid and mixtures of these compounds; sucrose octaoleate is a particularly preferred compound.

The second component of the present invention is a sweetener which is included in an amount of from about 0.001% to about 5%, preferably from about 0.01% to about 1%, and most preferably from about 0.025% to about 0.5%, of the finished composition. The sweetener component used must have a relatively high potency (i.e., at least about 50 times the sweetness of glucose) in order to be effective in the compositions of the present invention; thus, standard natural sweeteners, such as sucrose, glucose, and fructose are not operable. Further, the sweetener must have at least some degree of lipid solubility at ambient temperatures. The lipid rate of solubility of the sweetener can be increased by pulverization (e.g., to a micro-fine, less than 10 μm state) and the lipid solubility increased through the use of emulsifiers, such as mono- or di-glycerides, known in the food art. Any sweetener which meets the criteria set forth herein may be used in the compositions of the present invention. In addition, mixtures of such sweeteners may be utilized. Examples of useful sweeteners include but are not limited to, synthetic alkoxy aromatics, such as Dulcin and P-4000; synthetic oximes, such as perilartine; synthetic sulfamic acids, such as acesulfame; peptides, such as aspartyl malonates and succanilic acids; dihydro-chalcones (see U.S. Pat. No. 3,743,716, Rizzi, et al., issued July 3, 1973, incorporated herein by reference), and, most preferably, saccharin (o-benzoic sulfimide).

The final required component in the compositions of the present invention is a flavorant; these materials are included at levels of from about 0.1% to about 5%, preferably from about 0.1% to about 1%, and most preferably from about 0.25% to about 0.75%, of the finished composition. The flavorant used may be natural or synthetic, but must be lipid soluble at ambient temperatures. Single flavorants or mixtures of such flavorants may be used. Although mint flavorants, especially peppermint, are preferred, flavorants of the other general types, such as fruit flavors, or vanilla and chocolate flavors, may also be used. Specific examples of flavors which may be included in the compositions of the present invention include, but are not limited to, oil of sweet birch, oil of spearmint, oil of wintergreen, anise oil, dill oil, celery seed oil, various citrus oils, including lemon, orange, lime, tangerine and grapefruit oils, clove oil, peppermint oil, cassia, carrot seed oil, cola concentrate, ginger oil, angelica oil, vanillin, and the like.

The compositions of the present invention may also optionally contain other components conventionally found in food or pharmaceutical compositions, in their art-established levels of use. Examples of such components include binders, bulking agents, vitamins, minerals, preservatives, anti-oxidants, starches, flour, milk or milk extracts, such as milk sugar or sodium caseinate, sweeteners or flavorants not falling within the definitions given above, vegetable proteins, protein hydrosylates, microbial proteins, yeast extracts, gelatin, vegetable gums, cocoa, chocolate, food acids, colorants, and mixtures of the foregoing.

In preparing the compositions of the present invention, the sweetener is solubilized in the oil or oil-like material, such as by heat and/or agitation, and the flavorant is then added in a manner so as not to lose its volatile components. Specifically, in one method of preparation, the base oil is warmed to a temperature of from about 100° F. to about 150° F. and a small amount of sweetener is added, with agitation. The agitation and heat are continued until the sweetener is solubilized in the oil. After cooling the mixture to ambient temperature, the desired level of flavorant is added and mixed until homogeneous. When the oily material is a pharmaceutical agent, it is, of course, necessary to be certain that the warming step used in preparation of the composition will not adversely affect the pharmaceutical properties of that compound.

When using the composition of the present invention in a pharmaceutical composition, two broad approaches may be used: (1) a safe and effective amount of an oil-like pharmaceutical agent may be substituted in whole or in part for the edible oil or oil-like component; or (2) the compositions of the present invention may be formulated using conventional edible oil materials and a safe and effective amount of a lipid soluble pharmaceutical agent may be added to that finished composition.

Unless otherwise specified all percentages and ratios given herein are by weight.

The following non-limiting examples illustrate the compositions and the process for making those compositions encompassed by the present invention.

EXAMPLE I

Using the procedure described below, compositions of the present invention, as given in the following table, were prepared.

| Formulation No. | Components and Weights (grams) | | | |
|---|---|---|---|---|
| | Vegetable Oil (Crisco ®) | Saccharin | Peppermint Concentrate[1] | Peach Flavor[2] |
| 1 | 120 g | 0.06 g | 3 g | — |
| 2 | 120 | 0.06 | 2 | — |
| 3 | 120 | 0.06 | 1 | — |
| 4 | 50 | 0.025 | — | 5 drops |

[1] A mixture of 40 g vegetable oil (Crisco ® Oil, sold by The Procter & Gamble Company, Cincinnati, Ohio) and 10 g artificial peppermint flavor (Takasago, No. G-9586(l) o/s).
[2] Supplied by Edlong, natural and artificial peach flavor No. 5518 (oil soluble).

In each case, the vegetable oil component was heated to a temperature of about 140° F. and stirred. Saccharin (o-benzoic sulfimide) was pulverized manually with a mortar and pestle, to enhance it dissolution, and was added to the warm oil with continued agitation. Dissolution of the saccharin appeared complete after about 30 minutes and the mixture was allowed to cool to ambient temperature. The flavor was then added to the oil mixture with agitation which was continued until the mixture was homogeneous.

All of the compositions which included the peppermint flavoring were found to be very palatable, exhibiting a non-oily taste and mouthfeel. The peach flavored sample was also found to be palatable but had a slightly oily mouthfeel. Formulation of the compositions, described above, but without the saccharin component resulted in a composition which was not considered to be palatable, having a very oily taste and mouthfeel. A similar result was obtained when the flavorant component was not included.

When other mild fruit flavors, such as strawberry or lemon, are substituted for the peach flavor, substantially similar results are obtained. Similar results are also obtained when the saccharin is replaced, in whole or part, by Dulcin, P-4000, Perilartine, Acesulfame, dihydrochalcones, aspartyl malonates, or mixtures of these compounds.

When polyol fatty acid esters having at least 4 fatty acid groups, each fatty acid having from about 8 to about 22 carbon atoms, such as sucrose octaoleate, are substituted, either partially or completely, for the Crisco oil component in the example above, substantially similar results are found.

EXAMPLE II

A larger batch of a peppermint flavor variation of the present invention was formulated as follows:

| Component | Weight (grams) |
| --- | --- |
| Vegetable Oil (Crisco ®) | 11,000 |
| Flavor* | 55.0 |
| Saccharin | 5.5 |

*Takasago, Artificial Peppermint Flavor, No. G-9586(L) o/s.

The vegetable oil was heated, with mechanical agitation, to a temperature of about 140° F. in a stainless steel container. Saccharin, manually pulverized using a mortar and pestle, was then added to the vessel. Agitation and heating were maintained until the saccharin was fully solubilized, about 4 hours later. An inert gas purge of the vessel was maintained while the oil was warm to prevent oxidation. After cooling to room temperature, the flavoring component was added and mixed until homogeneous. The resulting composition was pleasant tasting and did not have an oily taste or mouthfeel.

Substantially similar results are obtained where the vegetable oil in the above example is replaced, in whole or in part, with corn oil, soybean oil, sunflower oil, safflower oil, cottonseed oil, palm kernel oil, rapeseed oil or mixtures of these materials.

What is claimed is:

1. A liquid pharmaceutical composition in oral dosage from comprising from about 25% to about 99.9% of an edible oil or oil-like pharmaceutical agent selected from polyol fatty acid esters having at least 4 fatty acid ester groups, such fatty acid having from about 8 to about 22 carbon atoms; made more palatable by incorporating in said pharmaceutical composition from about 0.001% to about 5% of a highly potent, lipid soluble sweetener, and from about 0.1% to about 5% of a lipid soluble flavorant.

2. A composition according to claim 1 wherein the sweetener is selected from the group consisting of saccharin, alkoxy aromatics, oximes, sulfamic acids, dihydrochalcones, aspartyl malonates, succanilic acids, and mixtures thereof.

3. A composition according to claim 2 which comprises from about 0.01% to about 1% of said sweetener.

4. A composition according to claim 3 wherein the sweetener is saccharin.

5. A composition according to claim 3 which comprises from about 0.1% to about 1% of the flavorant.

6. A pharmaceutical composition according to claim 1 wherein the flavorant is a natural or artificial mint flavor.

7. A pharmaceutical composition according to claim 6 wherein said flavorant is a natural or artificial peppermint flavor.

8. A pharmaceutical composition according to claim 1 which comprises from about 0.25% to about 0.5% of the sweetener.

9. A pharmaceutical composition according to claim 8 which comprises from about 0.25% to about 0.75% of the flavorant.

10. A pharmaceutical composition according to claim 9 wherein the pharmaceutical agent is sucrose octaoleate.

11. A process for preparing an edible liquid composition according to claim 1 wherein the sweetener component is solubilized in the edible oil or oil-like material and the flavorant is subsequently added to this mixture in a manner so as not to lose the volatile components contained in said flavorant.

* * * * *